US011580879B2

(12) United States Patent
Hadad et al.

(10) Patent No.: US 11,580,879 B2
(45) Date of Patent: Feb. 14, 2023

(54) SYSTEMS AND METHODS FOR GENERATING PERSONALIZED NUTRITIONAL RECOMMENDATIONS

(71) Applicant: MEDTRONIC MINIMED, INC., Northridge, CA (US)

(72) Inventors: Yaron Hadad, Los Gatos, CA (US); Jonathan Lipnik, Ramat Gan (IL); Ido Cohn, Herzelia (IL)

(73) Assignee: MEDTRONIC MINIMED, INC., Northridge, CA (US)

( * ) Notice: Subject to any disclaimer, the term of this patent is extended or adjusted under 35 U.S.C. 154(b) by 980 days.

(21) Appl. No.: 16/265,939

(22) Filed: Feb. 1, 2019

(65) Prior Publication Data

US 2019/0244541 A1 Aug. 8, 2019

Related U.S. Application Data

(63) Continuation of application No. 13/784,845, filed on Mar. 5, 2013, now abandoned.

(51) Int. Cl.
*G09B 19/00* (2006.01)
*G16H 20/60* (2018.01)

(52) U.S. Cl.
CPC ......... *G09B 19/0092* (2013.01); *G16H 20/60* (2018.01)

(58) Field of Classification Search
None
See application file for complete search history.

(56) References Cited

U.S. PATENT DOCUMENTS

| 7,882,150 | B2 | 2/2011 | Badyal |
| 8,376,750 | B1 | 2/2013 | Murphy-Aniceto et al. |
| 8,690,578 | B1* | 4/2014 | Nusbaum ............... G16Z 99/00 |
| | | | 705/2 |
| 2006/0064447 | A1* | 3/2006 | Malkov ............... G16H 20/60 |
| | | | 708/200 |

(Continued)

OTHER PUBLICATIONS

U.S. Non-Final office Action dated Jul. 31, 2015 in U.S. Appl. No. 13/784,845.

(Continued)

*Primary Examiner* — Phirin Sam
(74) *Attorney, Agent, or Firm* — Weaver Austin Villeneuve & Sampson LLP

(57) ABSTRACT

An algorithm and method to provide personal recommendations for nutrition based on preferences, habits, medical and activity profiles for users, and constraints. The algorithm can also be fed and takes into account real-time feedback from the user. The method allows creating a personal nutritional schedule based on a set of constraints, which are solved using an optimization algorithm to find the diet best fitting each user. The method also includes analyzing a single user by applying various statistical techniques, enabling the algorithm to infer the user's preferences and updating of the constraints, analyzing and clustering of the general user population based on statistical principles, giving the algorithm insightful information and allowing improved performance by means of "machine-learning," and creating a list of recommended food items/recipes to help users live a balanced, healthier lifestyle.

33 Claims, 8 Drawing Sheets

(56) References Cited

U.S. PATENT DOCUMENTS

| | | | |
|---|---|---|---|
| 2006/0122468 A1* | 6/2006 | Tavor | G16H 20/60 |
| | | | 600/300 |
| 2007/0141540 A1 | 6/2007 | Borg | |
| 2010/0136508 A1 | 6/2010 | Zekhtser | |
| 2011/0009708 A1 | 1/2011 | Boyes | |
| 2011/0125783 A1 | 5/2011 | Whale et al. | |
| 2012/0179665 A1 | 7/2012 | Baarman et al. | |
| 2013/0108993 A1 | 5/2013 | Katz | |
| 2014/0099614 A1 | 4/2014 | Hu et al. | |
| 2014/0255882 A1 | 9/2014 | Hadad et al. | |
| 2015/0093725 A1* | 4/2015 | Baarman | G09B 5/00 |
| | | | 600/300 |
| 2016/0232624 A1* | 8/2016 | Goldberg | G06Q 30/08 |
| 2021/0272474 A1* | 9/2021 | Geronimo-Button | |
| | | | G16H 20/70 |

OTHER PUBLICATIONS

U.S. Non-Final Office Action dated Oct. 7, 2014 in U.S. Appl. No. 13/784,845.

* cited by examiner

| | Monday 19/3/2012 | Tuesday 20/3/2012 | Wednesday 21/3/2012 | Thursday 22/3/2012 | Friday 23/3/2012 | Saturday 24/3/2012 | Sunday 25/3/2012 |
|---|---|---|---|---|---|---|---|
| 7 days-of-the-week 120 | Rest day | Power workout day | Aerobic workout day | Rest day Treat day! | Aerobic workout day | Aerobic workout day | Rest day Treat day! |

Fig. 1

| 210 times | Monday 19/3/2012 | Tuesday 20/3/2012 | Wednesday 21/3/2012 | Thursday 22/3/2012 | Friday 23/3/2012 | Saturday 24/3/2012 | Sunday 25/3/2012 |
|---|---|---|---|---|---|---|---|
| 06:00 | | | | | | | |
| 08:00 | 1 egg, 2 slices whole bread, 1 tomato 1 orange | 1 cup cereal 1/2 cup soy milk | 2 slices whole bread 1 tomato 1 pear | 1 cup cereal 1/2 cup rice milk | 1 cup granola 1/2 cup yogurt | 1 egg, 2 slices whole bread, 1 tomato 1 orange | 1 cup cereal 1/2 cup soy milk |
| 10:00 | | | | | | | |
| 12:00 | 1 cup spaghetti, 1/2 cup tomato sauce 1/2 cup sliced veg 150 gr. Chicken breast | Hamburger, 2 cups boiled potatoes 1 cup boiled veg | 2 cups brown rice 1 cup chickpeas 1 cup fruit juice 1/2 cup sliced veg | 2 cups red lentils 1 large onion 1 cup fruit juice 1/2 cup sliced veg | 2 cups mashed potatoes 1 cup fried beans Fish fillet | 2 cups spaghetti 1 cup meat sauce 1/2 cup sliced veg | 2 cups green lentils 1 large onion 1 cup fruit juice 1/2 cup sliced veg |
| 14:00 | | | | | | | |
| 16:00 | 1 fruit | 1 protein bar | 1 fruit | 1 fruit | 1 fruit | 1 protein bar | 1 fruit |
| 18:00 | | Power workout | 10k run | | Spinning lesson | Power workout | |
| 20:00 | 2 slices whole bread + eggplant 1 yogurt | 2 cups couscous 1 cup beans 1 yogurt | 1 egg, 1 slice whole bread + hummus, 1/2 cup sliced veg | 1 cup mushroom soup 1 cup sliced veg 1 cup ice cream | 2 slices whole bread + eggplant, 1/2 cup sliced veg | 1 cup white rice 1 cup fried beans 1 yogurt | 1 cup mushroom soup 1 cup sliced veg 1 slice chocolate cake |
| 22:00 | | | | | | | |

7 days of the week 220

Fig. 2

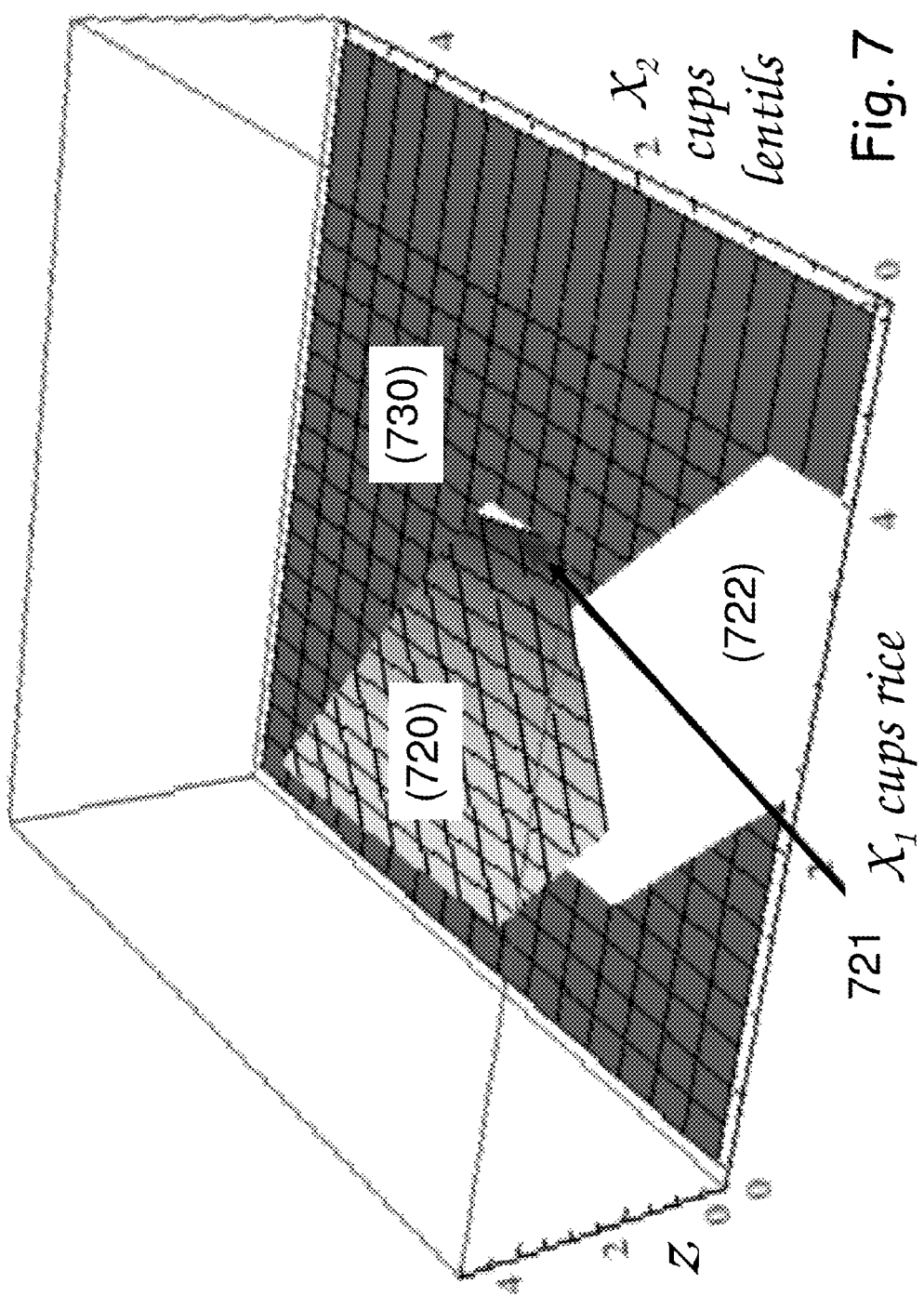

SYSTEMS AND METHODS FOR GENERATING PERSONALIZED NUTRITIONAL RECOMMENDATIONS

CROSS-REFERENCE TO RELATED APPLICATION

This application is a continuation application of U.S. application Ser. No. 13/784,845, filed on Mar. 5, 2013, which is incorporated herewith in its entirety.

FIELD OF THE INVENTION

The present invention relates to nutrition. More particularly, it is an algorithm that provides personalized meal plans for individuals in real-time, in order to help the general public to live a balanced & healthier lifestyle.

BACKGROUND OF THE INVENTION

There is currently no system known to the present inventors that produces nutritional recommendations based on personal needs either in academia or in the industry.
Diet Planning:
Today, diet planning is done in various ways. It may typically be classified in one of two categories: diets that are done and/or recommended by professional nutritionists, physicians or health experts and other "Crash Diet." The latter are diets that are performed by individuals who are seeking immediate results and often involve consumption of special foods, typically in the form of shakes; medicine, in the form of pills, or even extreme rapid changes in food consumption that deviate from the general guidelines given to the public by the authorities and can lead to malnutrition.
Statistically, most diets fail due to the enormous change in lifestyle they require from the dieter in a short time-scale. Indeed, most people don't have the willpower to completely change the habits they acquired over many years of eating in a certain way.
Nutritionists have their Drawbacks:
1. Human experts cannot continuously follow the person they are serving: their actual food consumption (if they divert from the proposed diet), physical activity and habits. Additionally, unless a nutritionist is meeting with his/her client on a daily basis, it is extremely difficult for a nutritionist to continuously change the proposed diet based on the user's reaction to it.
2. A human nutritionist works with a very basic set of rules, and does not take into account all the different factors. Indeed, the human body is a very complex system. This forces them to make simplifying assumptions to provide food recommendations, e.g. assuming that absorption of nutrients is linear, namely that a consumption of one nutrient does not affect the consumption of another. Nevertheless, this is known to be false in certain limits. For example, exaggerated consumption of animal protein requires affects the absorption of calcium in the body.
3. Most importantly, the output from a typical nutritionist session is a basic daily/weekly calendar with the food items the client should consume each day. This will definitely hinder the client's ability to follow the nutritional plan they receive from the nutritionist as the dieter won't always know what kind of changes he/she may make on-the-go.
4. A nutritionist is by definition a human participant, which is both expensive and error prone.
5. Many nutritionists have different training, which may lead to contradictory advice. For instance, one nutritionist may believe in a "low carbs" (Atkins) diet, while another may stick to a more conservative one.
6. Many people switch nutritionists over time, thus losing the consistency of their diet and making further failure in dieting even more probable.
Thus, it would be advantageous to provide more automated and timely nutritional assistance. Such assistance should complaint with health consideration and fully personal, while allowing changes in real-time based on the user's feedback.

SUMMARY OF THE INVENTION

It is a principal objective of the present invention to provide an automatic nutritionist. This virtual nutritionist works in real-time, and learns the user's habits and preferences to provide him with a personalized meal plan based on most restrictive and up-to-date health recommendations.
A method is disclosed to provide an application for personal recommendations for nutrition based on preferences, medical and activity profiles of a plurality of users, and constraints by applying an algorithm provided by "personal" modules, which interact with a single user and "global" modules, which analyze the data of all the users simultaneously. The method includes installing the application on computing devices belonging to a plurality of users and creating a personal nutritional schedule based on a set of constraints which are solved using an optimization algorithm. The method also includes analyzing a single user by applying various statistical techniques, enabling the algorithm to infer the user's preferences and updating of the constraints, analyzing and clustering of the general user population based on statistical principles, giving the algorithm insights and allowing improved performance by means of "machine-learning," and creating a list of recommended food items (either from recipes, raw foods, and even restaurants) to help each of the plurality of users live a balanced, healthier lifestyle.
The system's end product is a weekly meal-to-meal resolution nutritional schedule. The solution is tailored for each user individually and takes into account all aspects of the user's profile—medical, physical activity, cultural constraints, eating habits and culinary preferences.
The algorithm learns and adapts to the various user inputs. It can also improve its performance by crowd sourcing the data from the general user population.
It is important to state that the present invention emphasizes giving the highest value to the user, at least the same value he/she may receive from a nutritionist, while minimizing the deviation from his current way of life. This makes the automated nutritionist easier to use and follow to obtain better results, especially in the long term.
Another important aspect of this platform is that it provides a simple solution to people who don't follow the average diet and are not nutrition-savvy. For example, vegans (people who don't eat animal products) that do not understand the importance of proper consumption of legumes and green vegetables may suffer deficiencies in iron. This is automatically solved within the framework suggested here.
The Five Components of the Inventive Algorithm are:
1. The User Profiler, which employs the users' feedback to learn their habits and preferences. The User Profiler continuously improves the personalization of the algorithm's recommended diets.
2. The Diet Profiler, which creates a diet profile based on the user's profile. It generates a list of constraints that each diet for the user must satisfy. There are several different types of constraints, including nutrients constraints, health constraints, cultural constraints and other (see below).

3. The Diet Generator, which creates a list of recommended dishes for each day. The diet is calculated automatically using a selected optimization technique, such as integer, linear, quadratic, stochastic programming, dynamic programming or others, to find the diet with the highest ranking for each specific user, namely, this is the diet with the best value for the user based on his/her preference, goals, physique, working out habits and medical conditions. Thus, the optimization algorithm finds the optimal diet that satisfies the constraints given by the Diet Profiler.

Additionally, the diet generator allows the user to swap any dish in the diet by proposing alternative to it that also satisfy the same constraints and fit the specific meal, day and user's preferences.

4. The User Analyzer, which learns the users' habits to correct a diet in real-time and provides crowdsourcing for dietary/eating habits.

5. The Nutrition BI (Business Intelligence) System, which is a tool that allows research in nutrition. It employs usage data to derive insights about the general population's nutrition and health by searching for correlations between the different factors in the system, both the inputs and the outputs.

User Profiling

The interactive engine queries and analyzes the user's inputs efficiently, generating value for both the algorithm and the user.

Analyzing the user's input and behavior is one of the key ingredients for the platform's success. The platform gains insights from the user's input by the use of various statistical models to extrapolate the users preferences given their behavior. For example, one may calculate the probability of the user's affection for a certain food item based on the changes he/she made to the diet prescribed to him/her by the algorithm. The data acquired is used to improve the suggestions to the user, and thus increasing the quality of the results produced by the automated nutritionist.

Different clustering methods, such as K-NN, are used to find the different "preference type casts" and associate each user to the one they are closest to. As the number of possible preferences is infinite, clustering the different preference type casts can lead to interesting results and insights. Each user's meals can be offered to another user with similar taste enjoyed, improve the initial user input process, and provide a unique nutritional crowd sourcing platform. The methods used to solve the above modules are:

1. Collaborative filtering;
2. Baysian Network;
3. K-nearest Neighbor; and
4. Matrix Factorization.

There has thus been outlined, rather broadly, the more important features of the invention in order that the detailed description thereof that follows hereinafter may be better understood. Additional details and advantages of the invention will be set forth in the detailed description, and in part will be appreciated from the description, or may be learned by practice of the invention.

BRIEF DESCRIPTION OF THE DRAWINGS

In order to understand the invention and to see how it may be carried out in practice, a preferred embodiment will now be described, by way of a non-limiting example only, with reference to the accompanying drawings, in the drawings:

FIG. 1 is a table of the day-by-day recommended workout schedule for one week, constructed according to an exemplary embodiment of the present invention;

FIG. 2 is a table of the hourly, day-by-day recommended menu schedule for one week, constructed according to an exemplary embodiment of the present invention;

FIG. 7 is a graphic illustration of the diet generator phase with a third dimension for the objective function, constructed according to an exemplary embodiment of the present invention.

Figure 3A:
FIG. 3A and FIG. 3B show screenshot illustrations of the system's initial response to the user's initial input, constructed according to an exemplary embodiment of the present invention.

All the above and other characteristics and advantages of the invention will be further understood through the following illustrative and non-limitative description of preferred embodiments thereof.

DETAILED DESCRIPTION OF PREFERRED EMBODIMENTS

The principles and operation of a method and an apparatus according to the present invention may be better understood with reference to the drawings and the accompanying description, in which like numerals designate corresponding elements throughout, it being understood that these drawings are given for illustrative purposes only and are not meant to be limiting.

FIG. 1 is a table of the day-by-day 120 workout schedule for one week, constructed according to an exemplary embodiment of the present invention. A rest day means there is no physical workout. If the rest day is also a treat day, the user may be allowed an ice cream sundae, for example. A power workout day may mean there is some heavy lifting involved. An aerobic workout day may mean there is something like a "jazzercise" workout.

FIG. 2 is a table of the hour-by-hour 210, day-by-day 220 recommended menu for one week, constructed according to an exemplary embodiment of the present invention. The recommendation menu is created for personalized nutrition schedules. This platform is interfaced through multiple mobile and web clients.

This algorithm can be developed using many different programming languages on various servers. The choice of which should be mostly based on the preference and skill of the developers. In an exemplary embodiment of the algorithm, Java is used running with mySQL server and Amazon Web Services, while for the optimization algorithm the linear optimization method Simplex is used as a simple demonstration of the proposed technology.

The algorithm is an assembly of several modules—"personal" modules that interact with a single user and "global" modules that analyze the data of all users simultaneously.

At the heart of the algorithm lie several technologies:

1. The creation of the nutritional schedule is based on a set of constraints and an objective function that needs to be maximizes. It is solved using an optimization algorithm (e.g. linear optimization algorithm such as Simplex).

2. The analysis of a single user is done using various statistical techniques (such as collaborative filtering; Bayesian network and matrix factorization). This allows analysis and inference of the user's preferences and updating of the parameters. The statistical techniques used to solve the above modules may include:

3. The analysis and clustering of the general user population is also based on statistical principles and "large data" capabilities, giving the algorithm insights and allowing it to improve its performance. Different clustering methods, K-NN for example, are used to find the different "preference type casts" and associate each user to the one they are closest to. As the number of possible preferences is infinite, clustering the different preference type casts can lead to interesting results and insights.

Flow

1. On installation of the application onto a PC, iPhone or tablet, the user is asked several questions to determine his eating habits, physical and medical profile.

2. Next, the application queries the user about culinary preferences (note that this is not the same as eating habits). For this, the application takes on a game approach. The application tries to infer the user's tastes and habits according to a game where the user iteratively chooses one of two options on the screen. The user may be asked to choose between two choices—two food items, two typical meals, etc. In order for this approach to work the list of questions is assembled in a manner that will dissect the "preference space" in the optimal way, where each answer helps the algorithm benefit most from the previous question. For example, a possible first question may compare the user's preference of meat over nonmeat products, a preference that provides much insight into the user's diet), as opposed to the question that compares the user's preference of cauliflower over broccoli (gives little insight.

Figure 3B:
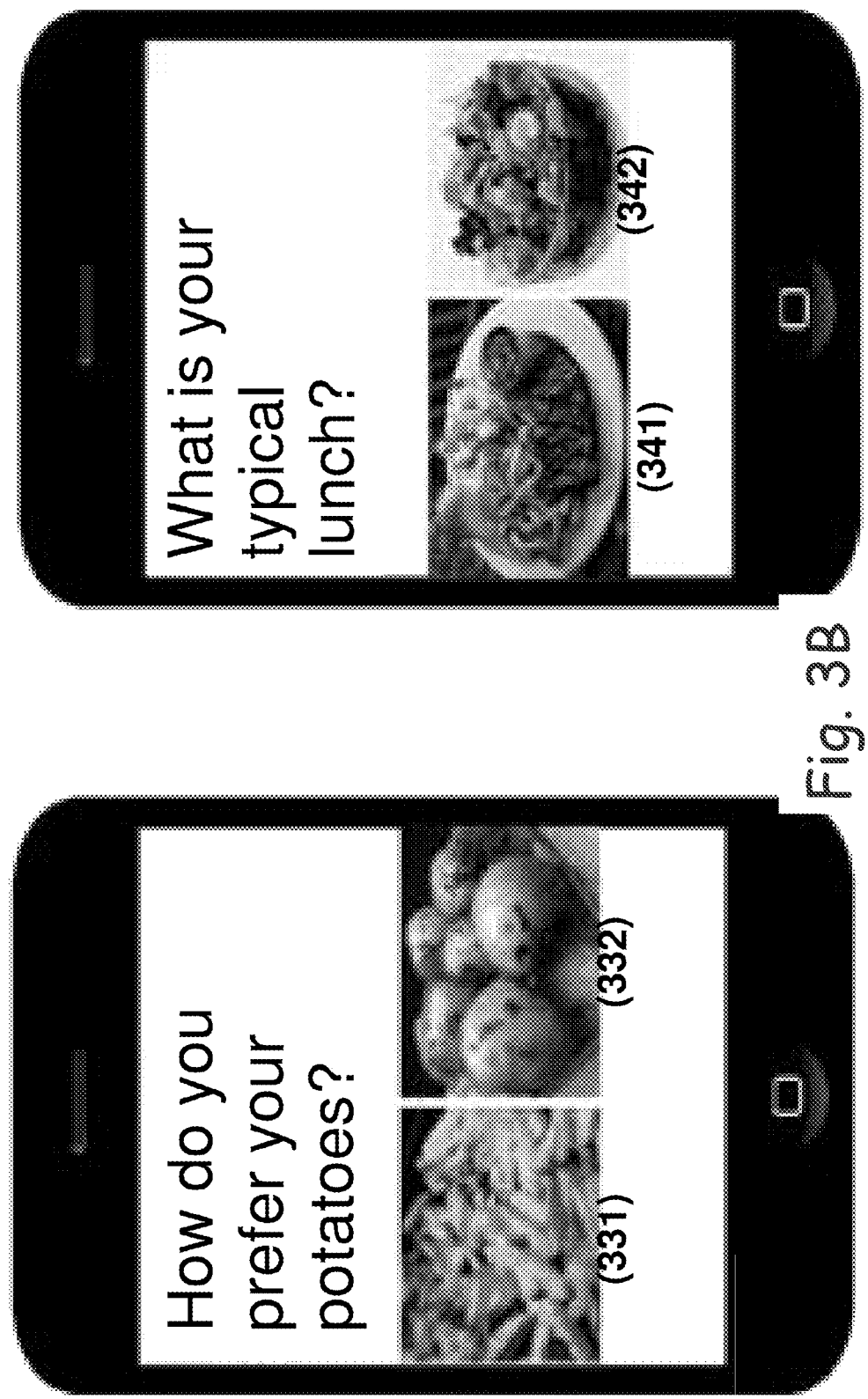

FIGS. 3A and 3B illustrate the use of simple 2 or 3 choice questions, constructed according to an exemplary embodiment of the present invention. The left side of FIG. 3A tests for various medical conditions 310. On the right side of FIG. 3A, the algorithm tests whether they are infatuated with meat 321, or if they usually eat a smaller healthier lunch 322.

The left screen shot 331 in FIG. 3B not only tests the user's love of French fries, but also the user's willingness to commit to a healthier diet. If the user chooses the right hand side image 332, the algorithm will try to create healthier meals, while if the image on the left hand side is chosen, the user will receive meals more to their liking, regardless of their healthiness. On the right side of FIG. 3B, the algorithm tests whether the user usually has a big lunch 341 vs. a small one 342, if they are infatuated with meat, or if they usually eat a smaller healthier lunch.

The algorithm searches for regularity in the answers. So for example, if the user doesn't pick meat in one of the questions, that won't necessarily mean he does not like meat. Only if several answers reveal the same pattern will the algorithm consider this a definite user eating habit.

An assortment of such questions can give the algorithm data that will help build a robust picture of the user's diet. This interface improves on the prior art for several reasons:

a. Humans are known to think in a relational way, and so comparing two or three options is easier than rating one.

b. A game interface engages users and allows them to input more data than was possible in the previous interfaces. As this is a less tedious task, users will be more willing to participate and answer more and more questions. Also, the user may stop inputting their preferences and return to the process later.

3. The nutrition scheduler gathers all the required information about the user needed to create a nutrition schedule—the user's activity profile (training activities schedule), medical profile (the user's medical condition), different data from a nutrition database, i.e., nutritional content of each food item and their relationships, and previously inputted user culinary preferences. Using this data, the first module creates a nutritional schedule—specifying which food items are to be consumed at each meal and at what quantity for the next week, with several options for substitution for each meal are provided.

4. Once the nutrition schedule is computed, it is provided to the user for the following week. During this period, the user may change food items, add/remove food items, and input what they have chosen to eat. The algorithm uses this input to adapt and improve its performance in its next suggestions to the user by considering which recommendations are being accepted and which are being ignored, and to what extent they are being ignored.

Technical Specifications

1. Nutritional Scheduler

The Nutritional Scheduler will be demonstrated by the use of linear optimization, although this is only a preferred embodiment of the patent and in no way should limit the current invention.

It is a 2-stage process:

a) Weekly diet calculator—Calculates the optimal weekly dish menu, consisting only of the amounts of each dish to be consumed in the weekly period.

Input:

The diet calculator relies on a multitude of inputs:

User eating habits

User culinary preferences

User physical goals (gain/reduce weight, waist size, etc. . . . )

User medical profile

User activity profile

Amount and type of user's activities

Nutrition Database

Nutritional values of each food item

Hierarchical association of each food item to a set of food groups

Association of each food item to a set of meals and meal types

Metric system between food items and food groups—distances between food items

The algorithm combines all constraints listed below with reference to FIG. 5 and creates a constraints matrix A, and a constraints vector b. A contains the nutritional amounts of each food item and each food group, and b contains the constraints amounts for each food group. These two data structures contain all the information on the user's nutritional, culinary and cultural constraints.

The solution vector x will contain the actual amounts of each food item the user is required to consume. Additionally, the problem of what to eat and how much is solved using an optimization function. Here the food items chosen are preferably closest to the user's known preferences. The algorithm reduces the problem of finding the proper diet to a linear problem of the form:

$$\min x = c^*x,$$

such that $A^*x <= b$, and c is a multiplier constant.

This linear optimization problem may be solved using the Simplex algorithm, however non-linear techniques may also be applied.

b) Weekly meal calculator—Spread the weekly dish menu calculated in the previous step into the different meals. This calculation may also solved using a Simplex algorithm:

Using the food item amounts calculated in the previous phase, the different constraints are inserted, but this time one for each possible meal, as opposed to one to each food item received in the previous phase. In the b vector, the amounts expected the user should consume in each meal are inserted, and also constraints to ensure the consumed amount of each food item will total the value calculated in the previous phase are inserted. The computation of the objective function is done stochastically to ensure diversity in the meals so that each food item will not be in every single meal). The stochastic algorithm is elaborated on hereinbelow.

The Weekly Meal Calculator has two special features:

i. Changing the Diet on the Fly:

When the user receives a meal recommendation, he may decide to change it. In such an occasion, the system finds a set of replacements that fits the users' preferences and habits while satisfying the constraints mentioned earlier. Moreover, the on-the-go feature also supports eating out. The user may also ask for food recommendations when eating out in two different ways: either an unlimited one, in which the algorithm locates local restaurants and dishes that fit the user's diet; or limited ones, in which the user is already in a certain restaurant, and may ask for the best dish fitting his diet from the ones available.

ii. Creating a Weekly Shopping List:

Once the user approved his weekly meal plan, the application may generate a shopping list of the required ingredients. This allows the user to purchase all the ingredients online to make it even easier and simpler to follow the nutrition schedule in order to increase compliance.

2. Single User Analyzer:

Embodiments of the present invention create a module that will be able to query and analyze the user's inputs efficiently, generating value to both the algorithm and the user. Analyzing the user's input and behavior is one of the key steps for the platform. In gaining insights from the user's input, different techniques are considered for optimizing the algorithm using this data. Stochastic models extrapolate the user's preferences given the patterns in their behavior using the different food item's relationships, then the probability of the user's affection for a certain food item is calculated from the changes he made to the diet prescribed for him by the algorithm. The data acquired is used to improve the suggestions to the user, and increase its value.

3. User Clustering and Data Analysis:

The final phase of the algorithm includes analyzing and clustering the platform's users. Different clustering methods, K-NN for example, are used to find the different "preference type casts" and associate each user to the one is closest to him. As the number of possible preferences is infinite, clustering the different preference type casts can lead to interesting results and insights. A user can be offered meals which another user with similar tastes enjoyed, thereby improving the initial user input process, and providing a unique nutritional crowd sourcing platform.

Exemplary embodiments include the full user input analysis and the ability to create recommendations based on this feedback. Additionally, it includes the full list of medical conditions that the algorithm can handle, giving more value to a wider user base. Also included is an analysis of the general population—trends and insights. Users are clustered, enabling users to get similar recommendations to those of other users in their cluster. This creates "nutrition crowdsourcing." This also involves finding interesting BI data—user segments, correlations between cause (diet) and effect (user feedback).

Figure 4:
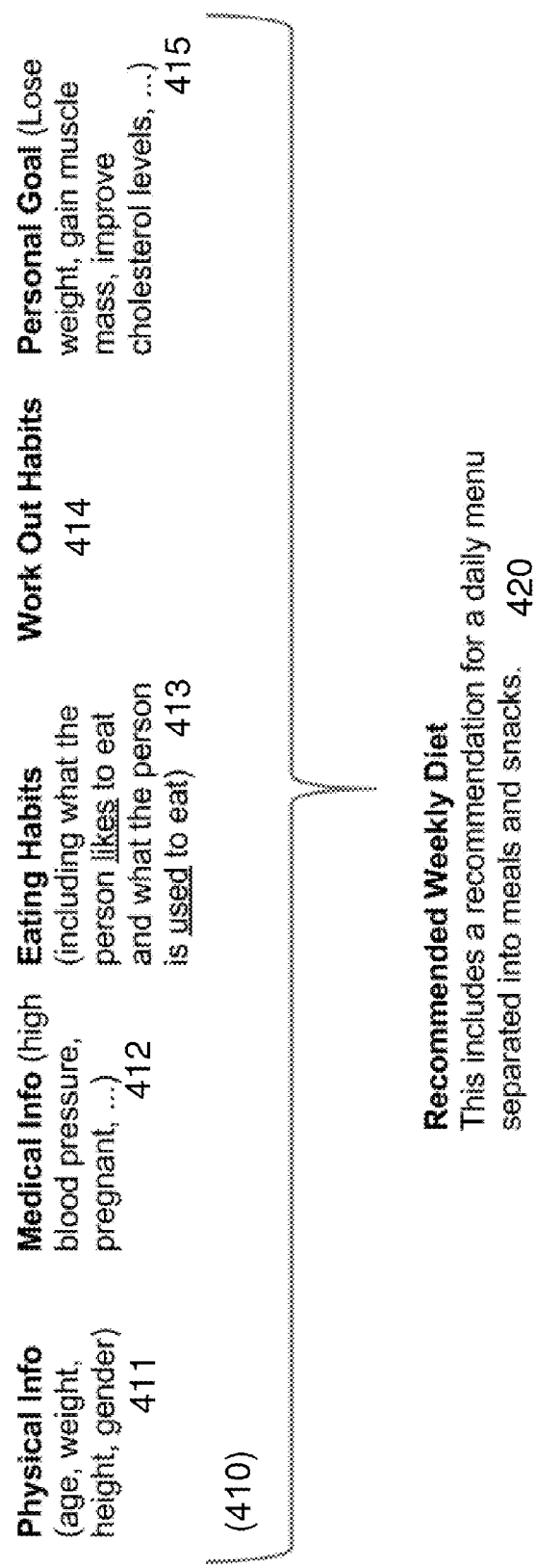
FIG. 4 illustrates the inputs and outputs of the interactive engine, constructed according to an exemplary embodiment of the present invention.

FIG. 4 illustrates the inputs and outputs of the interactive engine, constructed according to an exemplary embodiment of the present invention. Inputs 410 include physical info 411, medical info 412, eating habits 413, work out habits 414 and personal goals 415. The output is generally a recommended weekly diet 420.

Meanwhile, in the background the program is constantly collecting information by submitting simple questionnaires to the users. This information may be used to conduct studies on the effects of nutrition on well-being. Its results are then used to fine-tune the program for improved results and better dietary models. This will be used only once the results are verified by other studies by professional researchers in the field.

Approaching Nutrition Through Optimization

The following describes the goal and idea of approaching nutrition through optimization:

The Goal: To provide users with a diet recommendation that is healthy and will allow them to reach their goals, but at the same time making the diet as compatible as possible with their habits and preferences.

The Idea:

1. Turn Health Restrictions into Constraints:

These constraints are typically constraints on nutrients (for example, a 30-year old male should consume between 10 mg and 30 mg iron per day to be healthy. This is the linear constraint: 10 mg<total iron per day<30 mg). This guarantees that the program will only provide a diet that contains nutrients within a 'healthy' range that also fits the user's goals.

2. Turn the User's Eating Habits and Preferences into the Objective Function:

So maximizing the objective function is equivalent to finding the diet that is most compatible with the user's preferences.

Other nonlinear constraints may be included as well. For example, it is known that high consumption of animal protein increases calcium loss in the urine, and therefore the constraint on calcium and animal protein should depend on each nonlinearly.

The two segments of the meal recommendation algorithm are:

The Diet Generator: Provide a list of food items and/or recipes that should be consumed by the user for each day of the week. This already takes into account the user's habits, goals and physical information.

The Meal Separator: Separate each daily diet into well-portioned meals and their recommended eating time.

However, in practice there are two more parts that work in the background by considering inputs from the user showing what he is eating and what his workout activities are:

The Diet Profiler: Learns the user's eating and working out habits, together with the user's physical information to decide on the nutrients' constraints, plan the ideal meal size and eating time.

The Habits Learner: Correct the diet recommendation in real-time based on how the user follows the original diet recommendation. For example, if one ate pizza for dinner instead of a salad this might modify the diet recommendation for the coming days slightly.

Figure 5:
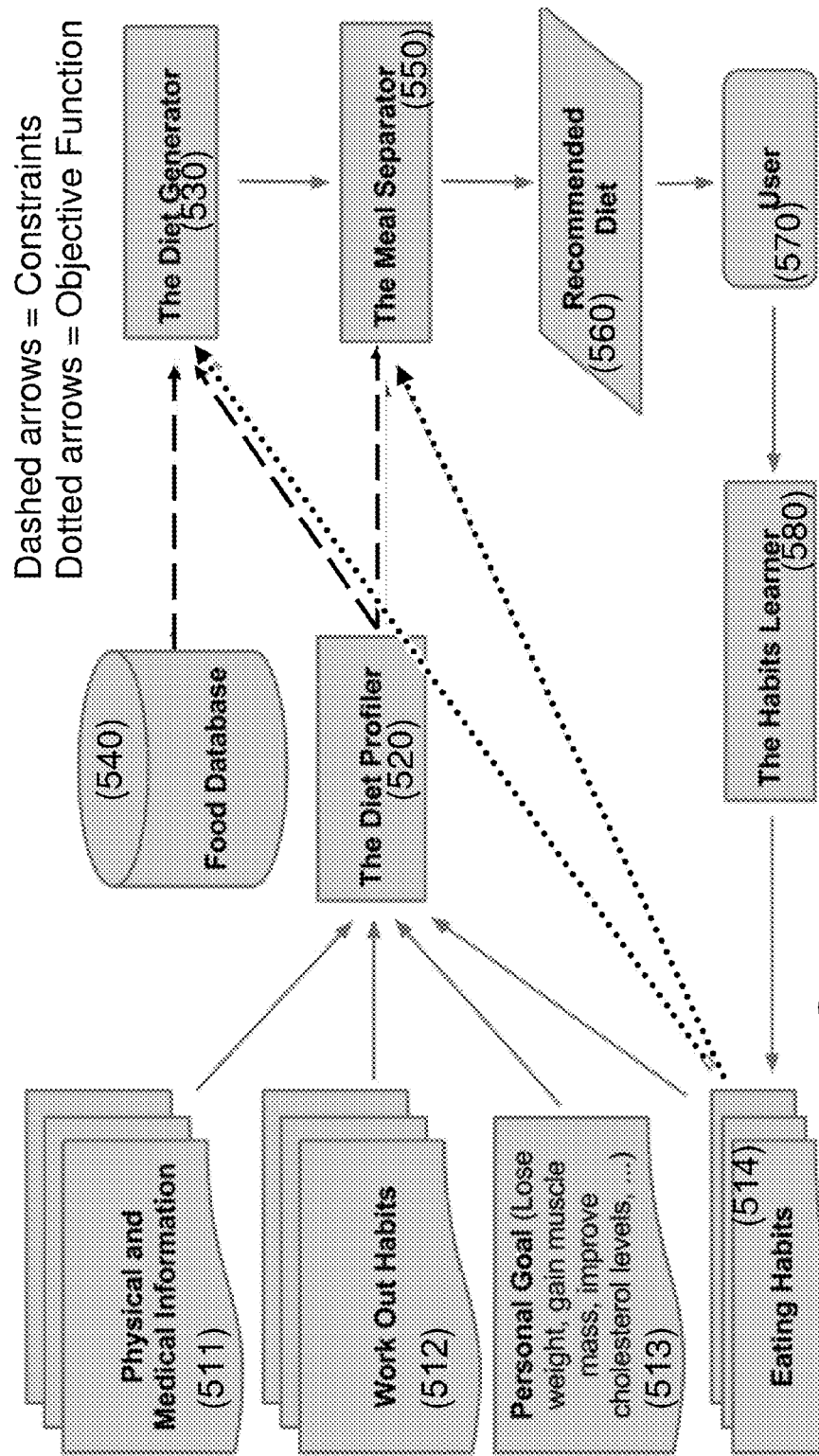
FIG. 5 illustrates the workflow provided by the meal recommendation portion of the algorithm of the interactive engine, constructed according to an exemplary embodiment of the present invention.

FIG. 5 illustrates the workflow of by the meal recommendation portion of the algorithm of the interactive engine, constructed according to an exemplary embodiment of the present invention. The workflow shows that physical and medical information 511, work out habits 512, personal goals 513 and eating habits 514 are all input to the diet profiler 520. Eating habits 514 are provided in the form of the objective function as inputs to both the diet generator 530 and the meal separator 550 and diet profiler 520 provides inputs in the form of constraints to both diet generator 530 and meal separator 550. The food database 530 also provides input to diet generator 530, and from there to meal separator 550, recommended diet 560, the user 570, the habits learner 580, each in sequence and then full-cycle back to eating habits 514.

The algorithm uses a linear optimization format for each of a set of days.

This requires constraints and an objective function.

There are three types of constraints:

Health constraints: they guarantee that the diet is healthy enough in terms of the different food groups and their diversity.

Examples:
>=2 fruits per day
>=1 serving of whole grains.

Nutrient constraints: these make sure the diet satisfies the governmental recommendations on nutrients.

Example:
>=10 mg iron, for a 30-year male per day

Cultural constraints: The previous constraints make sure the diet is healthy. The cultural constraints make sure the diet will make sense culturally, to avoid getting results that don't make any sense, like eating 1 kg of sprouts a day which no one will follow . . . .

Examples:
Total amount of bananas per day<=3,
Total amount of sprouts<=50 grams.

Thus, the constraints make sure the diet will be healthy and will make sense culturally/traditionally. The objective function makes the diet compatible with the eating habits and preferences of the user. The objective function is computed for each one of the days and takes into account the previous days.

For example: If there are N food items, the optimization algorithm turns the problem into a geometry problem involving a shape sitting in an N+1 dimensional space. More than 3 dimensions is typically impossible to visualize. However, in FIG. 6 there is an example of only 2 food items that are possible to visualize. The food items are brown rice $X_1$ and lentils $X_2$. This is not supposed to be a realistic case, but a case in which to demonstrate the geometry in 3 dimensional space to develop some intuition for the overall process.

Consider only three constraints, one of each type:
A health constraint: consumption of at least one serving of whole grain per day.
A nutrient constraint: total calories consumption should be between 500 and 1,000 calories a day.
A cultural constraint: the recommended diet should not contain more than 4 cups of rice.

Figure 6:
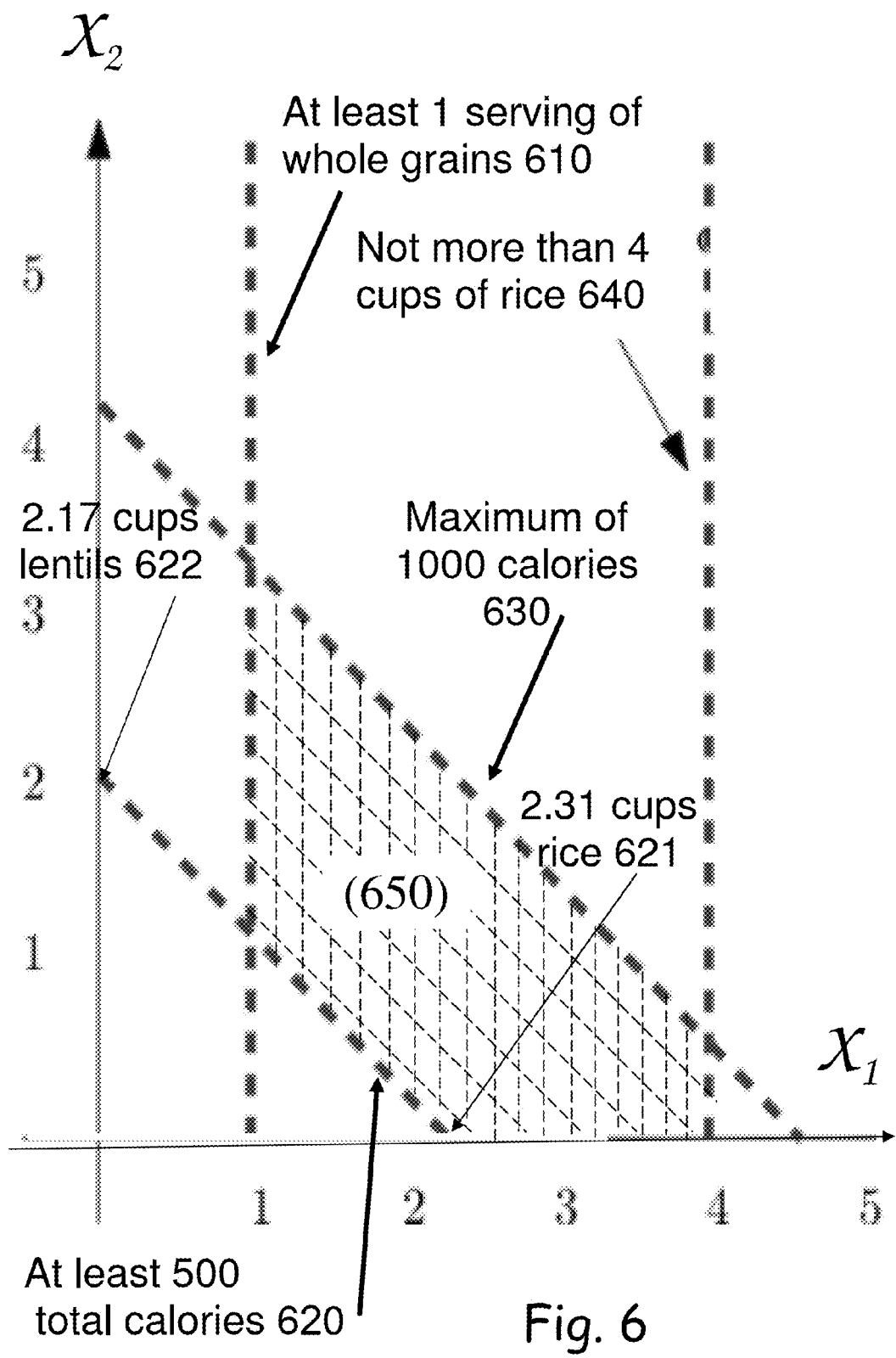
FIG. 6 is a graphic illustration of the diet generator phase of the algorithm of the interactive engine, constructed according to an exemplary embodiment of the present invention.

FIG. 6 is a graphic illustration of the diet generator phase of the algorithm of the interactive engine, constructed according to an exemplary embodiment of the present invention. $x_1$=amount of recommended rice. $x_2$=amount of recommended lentils. Both are measured in cups. A food recommendation corresponds to a choice of $x_1$ and $x_2$. Geometrically, a food recommendation corresponds to picking a point in this two dimensional space.

The health constraint: the recommended diet must contain at least one serving of whole grain per day 610. This means that the chosen point has to be right of the line 610.

The nutrient constraint: Total calories consumption should be between 500 and 1,000 calories a day. One has to eat at least 2.31 cups of rice to consume 500 calories. This provides one point in the plane 621. Similarly, one needs to eat at least 2.17 cups of lentils to consume 500 calories. This provides a second point in the plane 622. These 2 points define the line for at least 500 calories 620. One has to eat at least 4.62 cups of rice to consume 1000 calories. This provides one point in the plane, and one needs to eat at least 4.34 cups of lentils to consume 1000 calories. Again, this provides a second point in the plane, and these 2 new points define the line for at least 1000 calories 630.

The cultural constraint: One would not like to have more than 4 cups of rice daily 640.

The result is a Simplex region 650, in which to look for a recommended diet. Such a diet is designed to be healthy enough, as it satisfies all the constraints merely by being in the allowed region. In order to determine the most suitable diet for the user for that specific day, another dimension is needed. The simplex algorithm is a popular algorithm for linear programming solutions.

The height of the point in 3D space is the objective function, which represents how much the user likes this specific diet. Again, each point represents a specific diet, or combination of foods. If the dishes are all the same for the user he has no preferences and the graph is flat. The objective of a linear programming problem will be to maximize or to minimize some numerical value.

FIG. 7 is a graphic illustration of the diet generator phase with a third dimension for the objective function, constructed according to an exemplary embodiment of the present invention. The Simplex region of FIG. 6 650 is now seen elevated and curved, with darker elements representing greater elevation from the original 722 segment of 2D $X_1,X_2$ plane 730. If the user likes rice very much, but doesn't like lentils so much, the graph will be higher as the number of rice cups is higher. If the user likes lentils very much, the graph will be higher as the number of lentils cups is higher. In practice, the user likes several dishes, and the result is an elevation map representing the user's taste in food.

The solution is the highest (darkest) point on the graph. The recommended diet for that day is about 3 cups of rice with about 1 cup of lentils.

The algorithm is developed with the following conditions. Note that there are other important features that the algorithm takes into account:

One does not recommend 0.87233 cups of rice, but an integer number of servings. So only solutions that are multiples of whole servings are considered.

The recommended diet is based on a database of recipes, so one always gets complete meal recommendations, and not just single food items.

The height of each point is chosen stochastically, based on a probabilistic model. This means that every time a diet recommendation is requested, a different diet is offered. Thus, the algorithm is in fact capable of supplying infinitely many different diets, each of which is healthy enough and fits the taste of the specific user.

As for diversity of food, some people like to eat the same thing every day, while others do not. This is easily taken into account. When the height of each point is chosen, food items that were already eaten by the user or recommended for previous days get a penalty that might lower them back down. This is based on how much the user likes to diversify that specific food item. The user can choose a 'diverse factor' for each food item/group using a bar in the actual app. So for example, if rice was recommended for Monday and the user doesn't like to eat rice everyday, the objective function will be low on rice for the following days (Tuesday, etc. . . . ) and the user will get other dishes than rice on those days.

The meal separator is a rather simple application of the first phase, the diet generator. On the meal separator the algorithm is run on each one of the meals separately, i.e. breakfast, lunch, etc., over the food items obtained in the first phase. Each meal has its own set of cultural constraints. For example, for breakfast there will be a constraint on the food items that are typically consumed. Cereals are common for breakfast, but a steak would be forbidden. And in addition, each meal has nutrient constraints as well, for example that each meal will contain sufficient calories, roughly 25% of the calories in each main meal, and 5-10% in each of the snacks. Then an objective function is computed in a very similar way to the first phase.

Having described the present invention with regard to certain specific embodiments thereof, it is to be understood that the description is not meant as a limitation, since further modifications will now suggest themselves to those skilled in the art, and it is intended to cover such modifications as fall within the scope of the appended claims.

What is claimed:

1. A computer-implemented method for assisting with a user's nutritional needs, the method comprising:
    obtaining, from a computing device, a plurality of physiological and food consumption inputs associated with the user, wherein the plurality of physiological and food consumption inputs associated with the user comprises: (a) historical food consumption data, (b) eating habits, (c) culinary preferences, (d) health or physical goals, (e) a medical profile comprising physical and medical information of the user, or (f) an activity profile comprising an amount or type of physical activities that the user engages in;
    obtaining, from a database, a food ontology comprising information on a plurality of different food items;
    generating a plurality of constraints specific to the user based on (1) the plurality of physiological and food consumption inputs and (2) the food ontology, wherein the plurality of constraints comprises (i) health constraints, (ii) nutrient constraints and (iii) dietary norms;
    applying the plurality of constraints to an optimization algorithm to generate a graphical visual object representative of a food space; and
    determining and recommending one or more optimal diets for the user, based on selection of one or more points on the graphical visual object within the food space that satisfy the plurality of constraints.

2. The method of claim 1, wherein the computing device comprises a mobile device, a tablet, or a personal computer associated with the user.

3. The method of claim 2, wherein said method is implemented via a mobile application installed on the mobile device.

4. The method of claim 1, wherein the food ontology comprises a hierarchical association of each food item to selected groups or categories of foods.

5. The method of claim 4, wherein the food ontology comprises a metric system between the plurality of food items and the selected groups or categories of foods.

6. The method of claim 5, wherein the metric system comprises different distances between the plurality of food items, and the distances are depicted visually within the food space on the graphical visual object.

7. The method of claim 1, wherein the food ontology comprises an association of each food item to a set of meals or meal types.

8. The method of claim 1, wherein the information on the plurality of different food items comprises nutritional information of each food item.

9. The method of claim 8, wherein the nutritional information of each food item comprises a nutritional value of the food item, and type or amount of nutrients in the food item.

10. The method of claim 1, wherein the one or more optimal diets comprises a list of food items recommended to be consumed by the user over a defined time period.

11. The method of claim 10, further comprising: apportioning the list of food items into a plurality of different meals and recommended eating times.

12. The method of claim 1, wherein the optimization algorithm is configured to adjust one or more of the constraints based on changes to one or more of the physiological and food consumption inputs.

13. The method of claim 12, wherein the changes to one or more of the physiological and food consumption inputs are detected or obtained from the computing device.

14. The method of claim 12, wherein the optimization algorithm is configured to determine, based on the adjustments to the one or more constraints, whether adjustments to the one or more optimal diets for the user is needed, or whether a new optimal diet is needed.

15. The method of claim 1, wherein the optimization algorithm is configured to dynamically modify the one or more optimal diets depending on how closely the user is following the recommended one or more diets.

16. The method of claim 1, wherein the optimization algorithm is configured to dynamically modify the one or more optimal diets based on feedback from the user on the recommended one or more diets, wherein the feedback is provided via the computing device.

17. The method of claim 1, wherein the graphical visual object representative of the food space is configured to be displayed on the computing device of the user or other computing devices.

18. The method of claim 17, wherein the selection of the one or more points on the graphical visual object within the food space is enabled by using the computing device(s) to select the one or more points.

19. The method of claim 1, wherein the food space comprises an N+1 dimensional space for N number of food items.

20. The method of claim 1, wherein the food space comprises a curved and/or elevation map representing the user's taste in different foods.

21. The method of claim 1, wherein different points within the food space represent different diets or combinations of foods.

22. The method of claim 21, wherein a height of a specific point within the food space represents the user's degree of liking or preference for a diet associated with the specific point.

23. The method of claim 21, wherein the graphical visual object comprises different visual shadings for points located at different heights within the food space.

24. The method of claim 1, further comprising:
determining and recommending a different optimal diet for the user each time a diet recommendation is requested by the user.

25. The method of claim 24, wherein the different optimal diets are based on stochastic selection of different points within the food space that satisfy the plurality of constraints.

26. The method of claim 1, wherein the culinary preferences comprise a diversity factor input by the user for one or more of food items of the plurality of different food items.

27. The method of claim 1, wherein the plurality of constraints comprise linear and/or nonlinear constraints.

28. The method of claim 1, wherein said method is configured to assist a plurality of users with their nutritional needs, the method further comprising:
clustering the plurality of users to define a plurality of groups having different dietary preferences or needs; and
associating each user with a group that is closest to said user, to thereby generate a nutritional crowd sourcing platform.

29. The method of claim 28, wherein the nutritional crowd sourcing platform comprises trends, insights, and food recommendations that are provided to the users in the plurality of groups based on their different dietary preferences or needs.

30. The method of claim 28, wherein the plurality of users are clustered into and associated with different groups using K-near neighbor (K-NN), collaborative filtering, a Bayesian network, or matrix factorization.

31. The method of claim 1, wherein the optimization algorithm is configured to calculate a probability of the user's preference for a specific food item based on changes that the user makes to the one or more recommended optimal diets.

32. A system for assisting a plurality of users with their nutritional needs, the system comprising:
a server in communication with a plurality of computing devices and a database; and
a memory storing instructions that, when executed by the server, causes the server to perform operations comprising:
obtaining, from each of the computing devices, a plurality of physiological and food consumption inputs associated with a user of the corresponding computing device, wherein the plurality of physiological and food consumption inputs associated with the user comprises: (a) historical food consumption data, (b) eating habits, (c) culinary preferences, (d) health or physical goals, (e) a medical profile comprising physical and medical information of the user, or (f) an activity profile comprising an amount or type of physical activities that the user engages in;
obtaining, from the database, a food ontology comprising information on a plurality of different food items;
generating, for each of the users, a plurality of constraints specific to the user based on (1) the plurality of physiological and food consumption inputs and (2) the food ontology, wherein the plurality of constraints comprises (i) health constraints, (ii) nutrient constraints and (iii) dietary norms;
applying the plurality of constraints to an optimization algorithm to generate a graphical visual object representative of a food space; and
determining and recommending one or more optimal diets for each of the users, based on selection of one or more points on the graphical visual object within the food space that satisfy the plurality of constraints.

33. A non-transitory computer-readable medium including instructions that, when executed by a server, cause the server to perform operations comprising:
obtaining, from each of a plurality of computing devices, a plurality of physiological and food consumption inputs associated with a user of the corresponding computing device, wherein the plurality of physiological and food consumption inputs associated with the user comprises: (a) historical food consumption data, (b) eating habits, (c) culinary preferences, (d) health or physical goals, (e) a medical profile comprising physical and medical information of the user, or (f) an activity profile comprising an amount or type of physical activities that the user engages in;
obtaining, from a database, a food ontology comprising information on a plurality of different food items;
generating, for each of the users, a plurality of constraints specific to the user based on (1) the plurality of physiological and food consumption inputs and (2) the food ontology, wherein the plurality of constraints comprises (i) health constraints, (ii) nutrient constraints and (iii) dietary norms;
applying the plurality of constraints to an optimization algorithm to generate a graphical visual object representative of a food space; and
determining and recommending one or more optimal diets for each of the users, based on selection of one or more points on the graphical visual object within the food space that satisfy the plurality of constraints.

* * * * *